(12) United States Patent
Cerna et al.

(10) Patent No.: US 9,135,497 B2
(45) Date of Patent: Sep. 15, 2015

(54) IDENTIFYING RANDOMLY DISTRIBUTED MICROPARTICLES IN IMAGES TO SEQUENCE A POLYNUCLEOTIDE

(75) Inventors: Michael D. Cerna, Austin, TX (US); James C. Nagle, Austin, TX (US); Qing Ruan, Austin, TX (US); Darren R. Schmidt, Cedar Park, TX (US); Lothar Wenzel, Round Rock, TX (US)

(73) Assignee: National Instruments Corporation, Austin, TX (US)

( * ) Notice: Subject to any disclaimer, the term of this patent is extended or adjusted under 35 U.S.C. 154(b) by 90 days.

(21) Appl. No.: 13/359,950

(22) Filed: Jan. 27, 2012

(65) Prior Publication Data

US 2013/0196330 A1    Aug. 1, 2013

(51) Int. Cl.
| | |
|---|---|
| G01N 33/48 | (2006.01) |
| G06K 9/00 | (2006.01) |
| C12Q 1/68 | (2006.01) |
| C12M 1/34 | (2006.01) |
| G06K 9/20 | (2006.01) |
| G06K 9/32 | (2006.01) |
| G06K 9/34 | (2006.01) |
| G06K 9/36 | (2006.01) |
| G06F 19/22 | (2011.01) |

(52) U.S. Cl.
CPC ........ G06K 9/00147 (2013.01); G06K 9/00577 (2013.01); *G06F 19/22* (2013.01)

(58) Field of Classification Search
CPC . G06K 9/00147; G06K 9/00577; G06K 9/00; G06F 19/22; C12Q 1/68; C12M 1/34
See application file for complete search history.

(56) References Cited

U.S. PATENT DOCUMENTS

| | | |
|---|---|---|
| 6,219,452 B1 | 4/2001 | Nair et al. |
| 6,222,940 B1 | 4/2001 | Wenzel et al. |
| 6,229,921 B1 | 5/2001 | Wenzel et al. |
| 6,370,270 B1 | 4/2002 | Nair et al. |
| 6,403,320 B1 | 6/2002 | Read et al. |
| 6,493,079 B1 | 12/2002 | Piacentini |
| 6,610,482 B1 | 8/2003 | Fodor et al. |
| 6,615,158 B2 | 9/2003 | Wenzel et al. |
| 6,646,243 B2 | 11/2003 | Pirrung et al. |
| 6,654,505 B2 | 11/2003 | Bridgham et al. |
| 6,665,066 B2 | 12/2003 | Nair et al. |
| 6,665,335 B1 | 12/2003 | Rajagopal et al. |
| 6,757,428 B1 | 6/2004 | Lin et al. |
| 6,807,305 B2 | 10/2004 | Rajagopal et al. |
| 6,820,032 B2 | 11/2004 | Wenzel et al. |
| 6,831,994 B2 | 12/2004 | Bridgham et al. |
| 6,882,958 B2 | 4/2005 | Schmidt et al. |
| 6,909,801 B2 | 6/2005 | Wenzel et al. |
| 6,917,710 B2 | 7/2005 | Rajagopal et al. |
| 6,944,331 B2 | 9/2005 | Schmidt et al. |
| 6,950,552 B2 | 9/2005 | Nair et al. |
| 6,959,104 B2 | 10/2005 | Rajagopal et al. |
| 6,963,425 B1 | 11/2005 | Nair et al. |
| 6,963,667 B2 | 11/2005 | Rajagopal et al. |
| 7,013,047 B2 | 3/2006 | Schmidt et al. |
| 7,034,831 B2 | 4/2006 | Wenzel et al. |
| 7,039,229 B2 | 5/2006 | Lin et al. |
| 7,046,842 B2 | 5/2006 | Lin et al. |
| 7,120,301 B2 | 10/2006 | Wenzel et al. |
| 7,127,100 B2 | 10/2006 | Wenzel et al. |
| 7,136,505 B2 | 11/2006 | Wenzel et al. |
| 7,139,432 B2 | 11/2006 | Wenzel et al. |
| 7,158,677 B2 | 1/2007 | Wenzel et al. |
| 7,160,735 B2 | 1/2007 | Dehlinger et al. |
| 7,166,538 B2 | 1/2007 | Doshita |
| 7,171,048 B2 | 1/2007 | Wenzel et al. |
| 7,212,673 B2 | 5/2007 | Wenzel |
| 7,233,699 B2 | 6/2007 | Wenzel et al. |
| 7,233,700 B2 | 6/2007 | Rajagopal et al. |
| 7,269,286 B2 | 9/2007 | Wenzel et al. |
| 7,291,504 B2 | 11/2007 | Seul |
| 7,340,089 B2 | 3/2008 | Nair et al. |
| 7,390,676 B2 | 6/2008 | Seul et al. |
| 7,397,956 B2 | 7/2008 | Wenzel et al. |
| 7,450,765 B2 | 11/2008 | Wenzel |

(Continued)

OTHER PUBLICATIONS

Shendure, "Accurate Multiplex Polony Sequencing of an Evolved Bacterial Genome," Science, vol. 309, pp. 1728-1732 and Supplement pp. 1-36, 2005.*
Shendure, "Next-generation DNA sequencing," Nature Biotechnology, vol. 26, pp. 1135-1145, 2008.*
Vanni, "Internet-Based Image Analysis Quantifies Contractile Behavior of Individual Fibroblasts inside Model Tissue," Biophysical J, vol. 84, p. 2715-2727, 2003.*

(Continued)

*Primary Examiner* — Eric S DeJong
*Assistant Examiner* — G. Steven Vanni
(74) *Attorney, Agent, or Firm* — Meyertons Hood Kivlin Kowert & Goetzel, P.C.; Jeffrey C. Hood; Joel L. Stevens (57) ABSTRACT

Performing sequencing of a polynucleotide. A first image of microparticles that are distributed in a random fashion on a substrate may be received. Each of the microparticles may include a plurality of similar oligonucleotides of the polynucleotide. A second image of the microparticles may be received. A plurality of first subportions of the first image may be determined. Each subportion may include a respective plurality of microparticles distributed in a random fashion. The second image may be analyzed to identify a plurality of second subportions in the second image. Each of the plurality of second subportions may correspond to a respective one of the plurality of first subportions. A plurality of the microparticles may be matched from the first and second images based on said analyzing. At least a portion of the sequence of nucleotides of the polynucleotide may be determined based on said matching.

25 Claims, 5 Drawing Sheets

(56) References Cited

U.S. PATENT DOCUMENTS

| | | |
|---|---|---|
| 7,575,865 B2 | 8/2009 | Leamon et al. |
| 7,615,345 B2 | 11/2009 | Seul |
| 7,630,560 B2 | 12/2009 | Wenzel |
| 7,668,376 B2 | 2/2010 | Lin et al. |
| 7,749,774 B2 | 7/2010 | Seul |
| 7,906,758 B2 | 3/2011 | Stults et al. |
| 7,936,928 B2 | 5/2011 | Wenzel |
| 8,071,393 B2 | 12/2011 | Seul |
| 8,124,402 B2 | 2/2012 | Seul |
| 2011/0268347 A1* | 11/2011 | Staker .......................... 382/151 |

OTHER PUBLICATIONS

Michael L Metzker, "Sequencing technologies—the next generation," Nature Reviews Genetics, AOP, published online Dec. 8, 2009, www.nature.com/reviews/genetics, 16 pages.

* cited by examiner

IDENTIFYING RANDOMLY DISTRIBUTED MICROPARTICLES IN IMAGES TO SEQUENCE A POLYNUCLEOTIDE

FIELD OF THE INVENTION

The present invention relates to the field of image processing, and more particularly to a system and method for identifying microparticles in a plurality of images to perform polynucleotide sequencing.

DESCRIPTION OF THE RELATED ART

Since the discovery of deoxyribonucleic acid (DNA), scientific research has proliferated in various areas, including chemical reactions associated with DNA and other polynucleotides, its relation with genetics, the genomes of various organisms, etc. Accordingly, there has been a large focus on determining the nucleotides of polynucleotides, often referred to as "sequencing". Initially, lengthy and costly processes were developed for performing DNA sequencing, e.g., by performing numerous chemical reactions to identify the terminal individual nucleotides of a DNA strand.

In recent years, faster processes for performing sequencing have been developed, e.g., by dividing a polynucleotide into a multitude of oligonucleotides and sequencing those oligonucleotides in parallel. For example, these oligonucleotides may be initially bound to microparticles and amplified, e.g., using polymerase chain reaction (PCR). However, as these newer sequencing techniques have been optimized, image analysis issues have arisen. Accordingly, improvements in image processing, e.g., for performing polynucleotide sequencing, are desired.

SUMMARY OF THE INVENTION

Various embodiments are presented of a system and method for identifying microparticles in a plurality of images to perform polynucleotide sequencing.

Initially, a first image of microparticles may be obtained or stored. The microparticles may be distributed in a random fashion on or within a substrate. Additionally, each microparticle may include a plurality of similar oligonucleotides of a polynucleotide that is desired to be sequenced. More specifically, the polynucleotide may have been initially divided into a plurality of oligonucleotides, e.g., using restriction enzymes, which were then attached to the microparticles and amplified. Accordingly, the oligonucleotides of each respective microparticle may be essentially identical, e.g., having some small variations due to errors in amplification. In one embodiment, the first image may be an initial image of the microparticles, e.g., prior to performing a series of chemical reactions to determine the sequence of nucleotides that form the polynucleotide.

The microparticles may be visually identifiable in the image based on sets or clusters of similar pixels. More specifically, within the image, a user or program (e.g., a machine vision program) may be able to identify particular clusters of pixels as corresponding to a single microparticle or to a set of microparticles based on the cluster pixels having a similar color (e.g., white against a black background), forming a particular shape (e.g., a circle), etc. Further descriptions of the microparticles within images refer to such clusters of pixels within the image.

Additionally, all of the microparticles may be visually distinguishable in the first image. For example, as discussed below, the first image may be used as a template or base image for determining or identifying particular microparticles in subsequent images. Thus, all of the microparticles within the area of the substrate captured by the first image may be identifiable in the first image. In some embodiments, the first image may represent the microparticles before they emit light (e.g., with no chemical reaction causing fluorescence) or after they emit light (e.g., where the image captures all of the microparticles fluorescing), as desired.

Later, a second image of the microparticles may be obtained or stored. In one embodiment, the second image of the microparticles may be received after one or more chemical reactions have been performed on the oligonucleotides. For example, the chemical reactions may cause oligonucleotides which have a terminal nucleotide of a certain type to fluoresce or emit light at a specific wavelength or wavelength band. Accordingly, the microparticles which have that type of terminal nucleotide may be highlighted (e.g., may have a brighter or different color than other microparticles) in the second image. For example, a chemical reaction may cause a fluorescing chemical to attach to oligonucleotides having a first type of nucleotide (e.g., a "T" nucleotide in DNA). Thus, in this example, the microparticles which are highlighted in the second image may have a terminal nucleotide of the first type.

In some embodiments, as a result of a plurality of such chemical reactions, each different type of terminal nucleotide may fluoresce in a different wavelength band. Accordingly, the second image may indicate the different types for each of the microparticles (and accordingly the plurality of similar oligonucleotides) by indicating the different wavelengths in the image, e.g., as different colors. Alternatively, an image may be obtained for each different nucleotide type, which would result in second, third, fourth, and fifth images for terminal nucleotides of a DNA sequence.

However, in the second image (or any subsequent image), the particular position, orientation, scale, etc. may not be the same as the first image. For example, the second image may be rotated by a certain amount, may have moved during the chemical reaction process, may be larger or smaller, etc. Accordingly, it may be difficult to determine which microparticles in the second image correspond to microparticles in the first image, which may be crucial to performing accurate sequencing.

Accordingly, a plurality of first subportions of the first image may be determined. Each subportion may include a respective plurality of microparticles distributed in a random fashion. More specifically, the method may recognize that in an image having a random distribution of microparticles (as may be the case for the captured images), a small portion (e.g., 1% or smaller) of the image may be unique. Accordingly, a plurality of these portions (e.g., 3-5 or more) may be initially determined in order to perform later matching of microparticles between the first image and later images.

More specifically, the second image may be analyzed to identify a plurality of second subportions in the second image which correspond to the plurality of first subportions. Any of various pattern matching techniques may be used to identify the subportions in the second image which match the determined subportions in the first image.

Once the analysis is complete, the microparticles of the first and second images may be matched based on the analysis. In one embodiment, the subportions may be used to align the second image to the first image. For example, the second subportions may be used to re-orient, re-scale, and/or move the second image so that it matches the position, orientation, and scale of the first image, e.g., by ensuring that the position and size of the second subportions match the position and size of the first subportions. After performing this procedure, the positions of the microparticles in the second image may match the positions of the same microparticles in the first image. For example, the first image may have a first scale and the second image may be rescaled to match the first scale. Similarly, the second image may be translated or rotated to match the position or orientation of the first image. However, the second image may not actually have to be resized or reoriented—for example, once the relationship is understood, a mathematical translation may be used to perform the matching rather than requiring a modification to the second image itself. Thus, the matching may be performed with or without modifying the second image, as desired.

After performing the matching, at least a portion of the sequence of nucleotides of the polynucleotide may be determined based on said matching. More specifically, for a single image which fluoresces for a single type of nucleotide, the method may determine which oligonucleotides have that type of nucleotide at their terminus by determining which microparticles are fluorescing. Where images are produced for each different type of nucleotide, the same process may be performed for each different image to determine the terminal nucleotide for every microparticle. Where multiple nucleotides fluoresce at different wavelengths in a same image, the various different nucleotides may be determined for each microparticle by determining the emitting wavelength for each microparticle.

Regardless of how the terminal nucleotides are determined for the microparticles/associated oligonucleotides, the overall process may be repeated for each new terminal nucleotide. More specifically, after identifying the terminal nucleotides, they may be cleaved (e.g., using a restriction enzyme) and the process may be repeated for the new terminal nucleotide to determine the next nucleotide in the sequence.

After the sequences of the oligonucleotides of the microparticles have been determined, the entire sequence of the polynucleotide may be determined from the sequences of the oligonucleotides. This sequencing step may be performed by performing overlap analysis of the oligonucleotides (where the polynucleotide was initially cut into several different sets of overlapping oligonucleotides, e.g., resulting in multiple iterations of sequencing) or by comparing the sequences to a polynucleotide standard or known similar sequence, e.g., corresponding to the same species from which the polynucleotide was extracted.

BRIEF DESCRIPTION OF THE DRAWINGS

A better understanding of the present invention can be obtained when the following detailed description of the preferred embodiment is considered in conjunction with the following drawings, in which:

FIGS. 4A-6 are exemplary Figures corresponding to the method of FIG. 3.

While the invention is susceptible to various modifications and alternative forms, specific embodiments thereof are shown by way of example in the drawings and are herein described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Incorporation by Reference

The following references are hereby incorporated by reference in their entirety as though fully and completely set forth herein:

U.S. Pat. No. 4,914,568 titled "Graphical System for Modeling a Process and Associated Method," issued on Apr. 3, 1990.

U.S. Pat. No. 6,219,628 titled "System and Method for Configuring an Instrument to Perform Measurement Functions Utilizing Conversion of Graphical Programs into Hardware Implementations," filed Aug. 18, 1997.

U.S. Pat. No. 7,210,117 titled "System and Method for Programmatically Generating a Graphical Program in Response to Program Information," filed Dec. 20, 2000.

U.S. Pat. No. 6,654,505 titled "System and Apparatus for Sequential Processing of Analytes", filed Jul. 17, 2001.

U.S. Pat. No. 6,831,994 titled "System and Apparatus for Sequential Processing of Analytes", filed Jul. 17, 2001.

U.S. Pat. No. 6,370,270, titled "System and Method for Sampling and/or Placing Objects Using Low Discrepancy Sequences", filed Aug. 27, 1999.

U.S. Pat. No. 6,219,452, titled "Pattern Matching System and Method Which Performs Local Stability Analysis for Improved Efficiency", filed Jan. 6, 1999.

U.S. Pat. No. 6,222,940, titled "Pattern Matching System and Method Which Detects Rotated and Scaled Template Images", filed Apr. 24, 2001.

Terms

The following is a glossary of terms used in the present application:

Memory Medium—Any of various types of memory devices or storage devices. The term "memory medium" is intended to include an installation medium, e.g., a CD-ROM, floppy disks 104, or tape device; a computer system memory or random access memory such as DRAM, DDR RAM, SRAM, EDO RAM, Rambus RAM, etc.; a non-volatile memory such as a Flash, magnetic media, e.g., a hard drive, or optical storage; registers, or other similar types of memory elements, etc. The memory medium may comprise other types of memory as well or combinations thereof. In addition, the memory medium may be located in a first computer in which the programs are executed, or may be located in a second different computer which connects to the first computer over a network, such as the Internet. In the latter instance, the second computer may provide program instructions to the first computer for execution. The term "memory medium" may include two or more memory mediums which may reside in different locations, e.g., in different computers that are connected over a network.

Carrier Medium—a memory medium as described above, as well as a physical transmission medium, such as a bus, network, and/or other physical transmission medium that conveys signals such as electrical, electromagnetic, or digital signals.

Programmable Hardware Element—includes various hardware devices comprising multiple programmable function blocks connected via a programmable interconnect. Examples include FPGAs (Field Programmable Gate Arrays), PLDs (Programmable Logic Devices), FPOAs (Field Programmable Object Arrays), and CPLDs (Complex PLDs). The programmable function blocks may range from fine grained (combinatorial logic or look up tables) to coarse grained (arithmetic logic units or processor cores). A programmable hardware element may also be referred to as "reconfigurable logic".

Hardware Configuration Program—a program, e.g., a netlist or bit file, that can be used to program or configure a programmable hardware element.

Graphical Program—A program comprising a plurality of interconnected nodes or icons, wherein the plurality of interconnected nodes or icons visually indicate functionality of the program. The interconnected nodes or icons are graphical source code for the program. Graphical function nodes may also be referred to as blocks.

The following provides examples of various aspects of graphical programs. The following examples and discussion are not intended to limit the above definition of graphical program, but rather provide examples of what the term "graphical program" encompasses:

The nodes in a graphical program may be connected in one or more of a data flow, control flow, and/or execution flow format. The nodes may also be connected in a "signal flow" format, which is a subset of data flow.

Exemplary graphical program development environments which may be used to create graphical programs include LabVIEW®, DasyLab™, DiaDem™ and Matrixx/SystemBuild198 from National Instruments, Simulink® from the MathWorks, VEE™ from Agilent, WiT™ from Coreco, Vision Program Manager™ from PPT Vision, SoftWIRE™ from Measurement Computing, Sanscript™ from Northwoods Software, Khoros™ from Khoral Research, SnapMaster™ from HEM Data, VisSim™ from Visual Solutions, ObjectBench™ by SES (Scientific and Engineering Software), and VisiDAQ™ from Advantech, among others.

The term "graphical program" includes models or block diagrams created in graphical modeling environments, wherein the model or block diagram comprises interconnected blocks (i.e., nodes) or icons that visually indicate operation of the model or block diagram; exemplary graphical modeling environments include Simulink®, SystemBuild™, VisSim™, Hypersignal Block Diagram™, etc.

A graphical program may be represented in the memory of the computer system as data structures and/or program instructions. The graphical program, e.g., these data structures and/or program instructions, may be compiled or interpreted to produce machine language that accomplishes the desired method or process as shown in the graphical program.

Input data to a graphical program may be received from any of various sources, such as from a device, unit under test, a process being measured or controlled, another computer program, a database, or from a file. Also, a user may input data to a graphical program or virtual instrument using a graphical user interface, e.g., a front panel.

A graphical program may optionally have a GUI associated with the graphical program. In this case, the plurality of interconnected blocks or nodes are often referred to as the block diagram portion of the graphical program.

Node—In the context of a graphical program, an element that may be included in a graphical program. The graphical program nodes (or simply nodes) in a graphical program may also be referred to as blocks. A node may have an associated icon that represents the node in the graphical program, as well as underlying code and/or data that implements functionality of the node. Exemplary nodes (or blocks) include function nodes, sub-program nodes, terminal nodes, structure nodes, etc. Nodes may be connected together in a graphical program by connection icons or wires.

Data Flow Program—A Software Program in which the program architecture is that of a directed graph specifying the flow of data through the program, and thus functions execute whenever the necessary input data are available. Data flow programs can be contrasted with procedural programs, which specify an execution flow of computations to be performed. As used herein "data flow" or "data flow programs" refer to "dynamically-scheduled data flow" and/or "statically-defined data flow".

Graphical Data Flow Program (or Graphical Data Flow Diagram)—A Graphical Program which is also a Data Flow Program. A Graphical Data Flow Program comprises a plurality of interconnected nodes (blocks), wherein at least a subset of the connections among the nodes visually indicate that data produced by one node is used by another node. A LabVIEW VI is one example of a graphical data flow program. A Simulink block diagram is another example of a graphical data flow program.

Graphical User Interface—this term is intended to have the full breadth of its ordinary meaning The term "Graphical User Interface" is often abbreviated to "GUI". A GUI may comprise only one or more input GUI elements, only one or more output GUI elements, or both input and output GUI elements.

The following provides examples of various aspects of GUIs. The following examples and discussion are not intended to limit the ordinary meaning of GUI, but rather provide examples of what the term "graphical user interface" encompasses:

A GUI may comprise a single window having one or more GUI Elements, or may comprise a plurality of individual GUI Elements (or individual windows each having one or more GUI Elements), wherein the individual GUI Elements or windows may optionally be tiled together.

A GUI may be associated with a graphical program. In this instance, various mechanisms may be used to connect GUI Elements in the GUI with nodes in the graphical program. For example, when Input Controls and Output Indicators are created in the GUI, corresponding nodes (e.g., terminals) may be automatically created in the graphical program or block diagram. Alternatively, the user can place terminal nodes in the block diagram which may cause the display of corresponding GUI Elements front panel objects in the GUI, either at edit time or later at run time. As another example, the GUI may comprise GUI Elements embedded in the block diagram portion of the graphical program.

Front Panel—A Graphical User Interface that includes input controls and output indicators, and which enables a user to interactively control or manipulate the input being provided to a program, and view output of the program, while the program is executing.

A front panel is a type of GUI. A front panel may be associated with a graphical program as described above.

In an instrumentation application, the front panel can be analogized to the front panel of an instrument. In an industrial automation application the front panel can be analogized to the MMI (Man Machine Interface) of a device. The user may adjust the controls on the front panel to affect the input and view the output on the respective indicators.

Computer System—any of various types of computing or processing systems, including a personal computer system (PC), mainframe computer system, workstation, network appliance, Internet appliance, personal digital assistant (PDA), television system, grid computing system, or other device or combinations of devices. In general, the term "computer system" can be broadly defined to encompass any device (or combination of devices) having at least one processor that executes instructions from a memory medium.

Measurement Device—includes instruments, data acquisition devices, smart sensors, and any of various types of devices that are configured to acquire and/or store data. A measurement device may also optionally be further configured to analyze or process the acquired or stored data. Examples of a measurement device include an instrument, such as a traditional stand-alone "box" instrument, a computer-based instrument (instrument on a card) or external instrument, a data acquisition card, a device external to a computer that operates similarly to a data acquisition card, a smart sensor, one or more DAQ or measurement cards or modules in a chassis, an image acquisition device, such as an image acquisition (or machine vision) card (also called a video capture board) or smart camera, a motion control device, a robot having machine vision, and other similar types of devices. Exemplary "stand-alone" instruments include oscilloscopes, multimeters, signal analyzers, arbitrary waveform generators, spectroscopes, and similar measurement, test, or automation instruments.

A measurement device may be further configured to perform control functions, e.g., in response to analysis of the acquired or stored data. For example, the measurement device may send a control signal to an external system, such as a motion control system or to a sensor, in response to particular data. A measurement device may also be configured to perform automation functions, i.e., may receive and analyze data, and issue automation control signals in response.

Automatically—refers to an action or operation performed by a computer system (e.g., software executed by the computer system) or device (e.g., circuitry, programmable hardware elements, ASICs, etc.), without user input directly specifying or performing the action or operation. Thus the term "automatically" is in contrast to an operation being manually performed or specified by the user, where the user provides input to directly perform the operation. An automatic procedure may be initiated by input provided by the user, but the subsequent actions that are performed "automatically" are not specified by the user, i.e., are not performed "manually", where the user specifies each action to perform. For example, a user filling out an electronic form by selecting each field and providing input specifying information (e.g., by typing information, selecting check boxes, radio selections, etc.) is filling out the form manually, even though the computer system must update the form in response to the user actions. The form may be automatically filled out by the computer system where the computer system (e.g., software executing on the computer system) analyzes the fields of the form and fills in the form without any user input specifying the answers to the fields. As indicated above, the user may invoke the automatic filling of the form, but is not involved in the actual filling of the form (e.g., the user is not manually specifying answers to fields but rather they are being automatically completed). The present specification provides various examples of operations being automatically performed in response to actions the user has taken.

Figure 1:
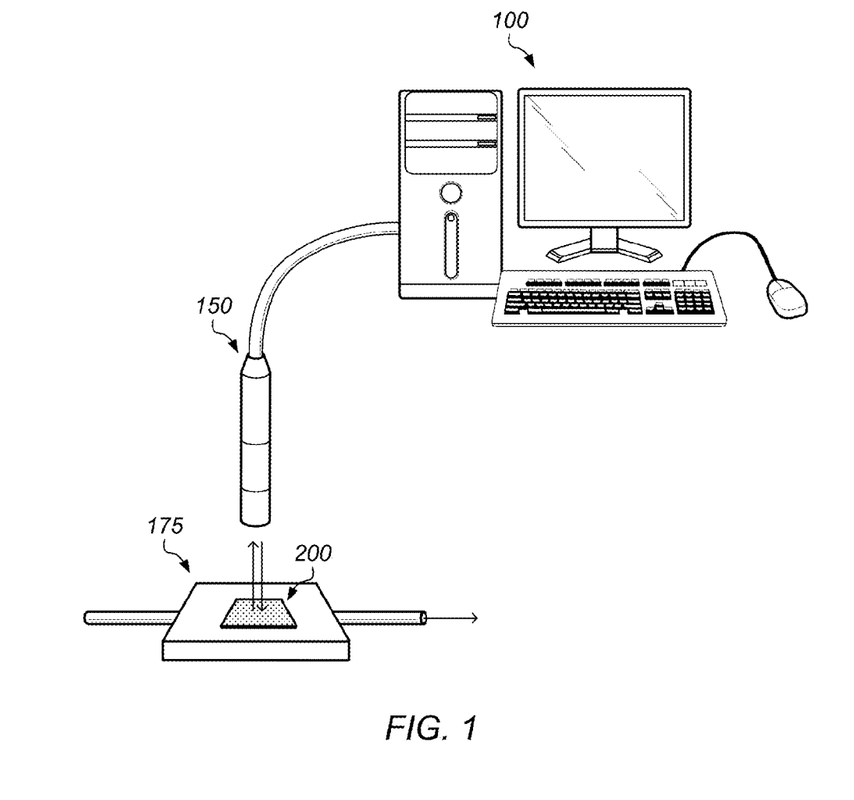
FIG. 1 illustrates an exemplary system for implementing various embodiments.
Figure 2:
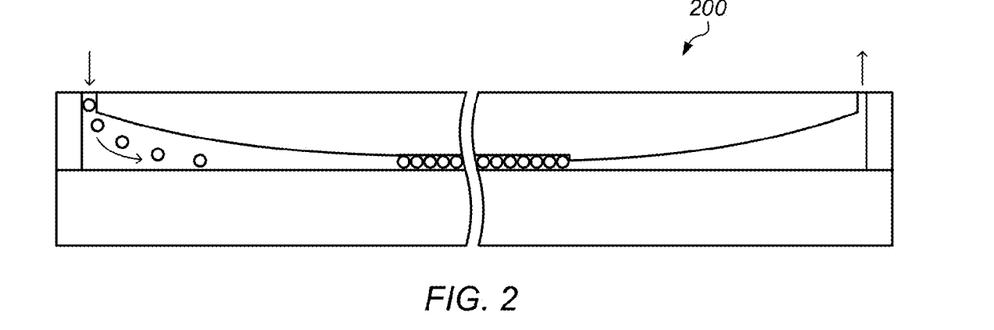
FIG. 2 illustrates an exemplary substrate including a plurality of microparticles.

FIGS. 1 and 2—Exemplary System and Apparatus

FIG. 1 illustrates an exemplary system configured to implement various embodiments described herein. More specifically, the exemplary system may be configured to perform the image processing described herein, e.g., to perform sequencing of a polynucleotide, such as a DNA strand. As shown, the exemplary system may include a computer system 100, an image acquisition apparatus 150, and a chemical reaction apparatus 175.

The computer system 100 may execute one or more control programs which may be executable to control the image acquisition apparatus 150 and/or the chemical reaction apparatus 175, e.g., to perform polynucleotide sequencing. More specifically, the computer system 100 may include at least one memory medium on which one or more computer programs or software components according to one embodiment of the present invention may be stored. For example, the memory medium may store one or more graphical programs which are executable to perform the methods described herein. Additionally, the memory medium may store a graphical programming development environment application used to create and/or execute such graphical programs. The memory medium may also store operating system software, as well as other software for operation of the computer system. Various embodiments further include receiving or storing instructions and/or data implemented in accordance with the foregoing description upon a carrier medium. In some embodiments, one or more programmable hardware elements may be implemented by the computer system 100, the image acquisition apparatus 150, and/or the chemical apparatus 175, e.g., to perform the methods described herein. These programmable hardware element(s) may be configured according to a graphical program, e.g., developed on the computer system 100, as discussed in U.S. Pat. No. 6,219,628, which was incorporated by reference above.

As also shown in FIG. 1, the computer system 100 may include a display device configured to display a graphical user interface (GUI) associated with the programs executing on the computer system 100. In some embodiments, the computer system may execute graphical programs and the display may display a GUI associated with the graphical programs as they are created and/or executed. The GUI may comprise any type of graphical user interface, e.g., depending on the computing platform.

As discussed below, the chemical reaction apparatus 175 may be configured to perform a plurality of chemical reactions on oligonucleotides loaded on microparticles within a reaction chamber 200, e.g., in order to perform sequencing of a polynucleotide from which the oligonucleotides originated. FIG. 2 illustrates an exemplary side view of a reaction chamber 200. As shown in FIG. 2, the reaction chamber 200 may be configured to receive a plurality of microparticles (e.g., having attached oligonucleotides) that may be blocked into a planar arrangement on a substrate within the reaction chamber 200. The chemical reaction apparatus 175 may be configured to introduce chemical reagents via an inlet and excrete chemical waste via an outlet to perform the plurality of chemical reactions. The computer 100 may control the chemical reactions performed by the chemical reaction apparatus 175.

Additionally, the image acquisition apparatus 150 (shown in FIG. 1 as a digital microscope) may be configured to acquire images of microparticles which act as the reaction site for the chemical reactions. For example, the chemical reactions may cause various oligonucleotides on the microparticles to fluoresce, which may allow for polynucleotide sequencing. Accordingly, the image acquisition apparatus 150 may capture images of these fluorescing microparticles (e.g., in the planar arrangement within the reaction chamber 200) and provide the images to the computer system 100. The computer system 100 may execute one or more programs (e.g., graphical programs) to perform the image analysis discussed herein, allowing the polynucleotide to be sequenced.

Further details regarding a similar system can be found in U.S. Pat. Nos. 6,654,505 and 6,831,994, which were incorporated in their entirety above. However, it should be noted that while the systems and sequences of chemical reactions of these patents may apply to present embodiments, the image processing embodiments discussed herein may differ significantly from those described in these incorporated patents.

Various ones of the components shown in FIG. 1 may be coupled over a network, such as a LAN (local area network), WAN (wide area network), the Internet, or an Intranet, among others. Additionally, the various control programs may be executed by a plurality of computer systems that communicate via such a network, as desired.

Figure 3:
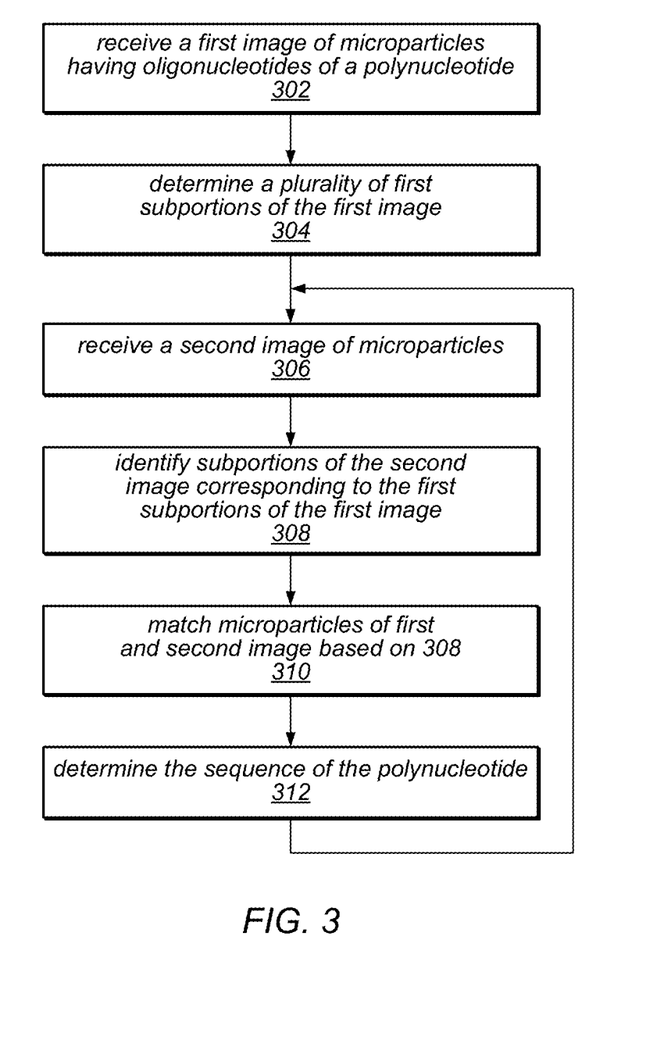
FIG. 3 is a flowchart diagram illustrating one embodiment of a method for identifying microparticles in a plurality of images to perform polynucleotide sequencing.

FIG. 3—Identifying Microparticles in Image to Perform Polynucleotide Sequencing

FIG. 3 illustrates a method for identifying microparticles in a plurality of images to perform polynucleotide sequencing. The method shown in FIG. 3 may be used in conjunction with any of the computer systems or devices shown in the above Figures, among other devices. In various embodiments, some of the method elements shown may be performed concurrently, in a different order than shown, or may be omitted. Additional method elements may also be performed as desired. As shown, this method may operate as follows.

Initially, in 302, a first image of microparticles may be obtained or stored. The microparticles may be distributed in a random fashion on or within a substrate, such as described above. Additionally, each microparticle may include a plurality of similar oligonucleotides of a polynucleotide that is desired to be sequenced. More specifically, the polynucleotide may have been initially divided into a plurality of oligonucleotides, e.g., using restriction enzymes, which were then attached to the microparticles and amplified, e.g., using polymerase chain reaction (PCR). The oligonucleotides may be attached to the microparticles in a manner that essentially results in a single oligonucleotide attaching to each microparticle, or at least no more than one is attached to each microparticle. Accordingly, after amplification, the oligonucleotides of each respective microparticle may be essentially identical, e.g., having some small variations due to errors in amplification.

The microparticles may be visually identifiable in the image based on sets or clusters of similar pixels. More specifically, within the image, a user or program (e.g., a machine vision program) may be able to identify particular clusters of pixels as corresponding to a single microparticle or to a set of microparticles based on the cluster pixels having a similar color (e.g., white against a black background), forming a particular shape (e.g., a circle), etc. Further descriptions of the microparticles within images refer to such clusters of pixels within the image.

In one embodiment, the first image may be an initial image of the microparticles, e.g., prior to performing a series of chemical reactions to determine the sequence of nucleotides that form the polynucleotide. Additionally, all of the microparticles may be visually distinguishable in the first image. For example, as discussed below, the first image may be used as a template or base image for determining or identifying particular microparticles in subsequent images. Thus, all of the microparticles within the area of the substrate captured by the first image may be identifiable in the first image. In some embodiments, the first image may represent the microparticles before they emit light (e.g., with no chemical reaction causing fluorescence) or after they emit light (e.g., where the image captures all of the microparticles fluorescing), as desired In 304, a plurality of first subportions of the first image may be determined. Each subportion may include a respective plurality of microparticles distributed in a random fashion. More specifically, the method may recognize that in an image having a random distribution of microparticles (as may be the case for the captured images), a small portion (e.g., 1%, 0.5%, 0.25%, 0.05%, or smaller) of the image may be unique. Accordingly, a plurality of these portions (e.g., 5) may be initially determined in order to perform later matching of microparticles between the first image and later images. These subportions may be referred to as "fingerprints" owing to their uniqueness. These fingerprints may be small and may not suffer much from rotation or scaling effects, in terms of later pattern matching, while large images are highly perturbed by those transformations. Additionally, their smallness in size may also mean that the image processing methods may allow them to be found more quickly in later images. Further, as discussed below, based on several of these fingerprints, the method may be able to quickly calculate rotation and scaling adjustments using fingerprint locations in later images, e.g., using as few as 3 or 5 fingerprints, although more may be used in further embodiments.

In 306, a second image of the microparticles may be obtained or stored. In one embodiment, the second image of the microparticles may be received after one or more chemical reactions have been performed on the oligonucleotides. For example, the chemical reactions may cause oligonucleotides which have a terminal nucleotide of a certain type to fluoresce or emit light at a specific wavelength or wavelength band. Accordingly, the microparticles which have that type of terminal nucleotide may be highlighted (e.g., may have a brighter or different color than other microparticles) in the second image. For example, a chemical reaction may cause a fluorescing chemical to attach to oligonucleotides having a first type of nucleotide (e.g., a "T" nucleotide in DNA). Thus, in this example, the microparticles which are highlighted in the second image may have a terminal nucleotide of the first type.

In some embodiments, as a result of a plurality of such chemical reactions, each different type of terminal nucleotide may fluoresce in a different wavelength band. Accordingly, the second image may indicate the different types for each of the microparticles (and accordingly the plurality of similar oligonucleotides) by indicating the different wavelengths in the image, e.g., as different colors. Alternatively, an image may be obtained for each different nucleotide type, which would result in second, third, fourth, and fifth images for terminal nucleotides of a DNA sequence.

However, in the second image (or any subsequent image), the particular position, orientation, scale, etc. may not be the same as the first image. For example, the second image may be rotated by a certain amount, may have moved during the chemical reaction process, may be larger or smaller, etc. Accordingly, it may be difficult to determine which microparticles in the second image correspond to microparticles in the first image, which may be crucial to performing accurate sequencing.

Accordingly, in 308, the second image may be analyzed to identify a plurality of second subportions in the second image which correspond to the plurality of first subportions. Any of various pattern matching techniques may be used to identify the subportions in the second image which match the determined subportions in the first image. For example, the pattern matching techniques discussed in the patents incorporated by reference above.

More specifically, the pattern matching techniques from U.S. Pat. Nos. 6,370,270, 6,219,452, and 6,222,940 may be used for matching portions of the second image to the subportions and/or for matching the first and second images. For example, low discrepancy sequences may be determined and then used to perform the pattern matching. Additionally, or alternatively, local stability analysis may be used within the low discrepancy sequences and/or for the subportions of the images discussed above. Additionally, the described rotation invariant pattern matching techniques may also be used, e.g., in conjunction with the local stability analysis.

In some embodiments, the second image may be modified in order to perform the matching of the subportions. For example, as discussed above, various ones of the microparticles may be fluorescing in the second image, which may interfere with the pattern matching process. Accordingly, the second image may be modified to remove the fluorescence (e.g., by applying a filter or lowering brightness/contrast, among other processes) so that the pattern matching may be more accurate and/or more efficient. However, this modified second image may not be used when determining the sequence of the polynucleotide, discussed below, since the fluorescence may indicate the presence of particular nucleotides.

Once the analysis is complete, in 310, the microparticles of the first and second images may be matched based on the analysis. In one embodiment, the subportions may be used to align the second image to the first image. For example, the second subportions may be used to re-orient, re-scale, and/or move the second image so that it matches the position, orientation, and scale of the first image, e.g., by ensuring that the position and size of the second subportions match the position and size of the first subportions. After performing this procedure, the positions of the microparticles in the second image may match the positions of the same microparticles in the first image. For example, the first image may have a first scale and the second image may be rescaled to match the first scale. Similarly, the second image may be translated or rotated to match the position or orientation of the first image. However, the second image may not actually have to be resized or reoriented—for example, once the relationship is understood, a mathematical translation may be used to perform the matching rather than requiring a modification to the second image itself. Thus, the matching may be performed with or without modifying the second image, as desired.

After performing the matching, in 312, at least a portion of the sequence of nucleotides of the polynucleotide may be determined based on said matching. More specifically, for a single image which fluoresces for a single type of nucleotide, the method may determine which oligonucleotides have that type of nucleotide at their terminus by determining which microparticles are fluorescing. Where images are produced for each different type of nucleotide, the same process may be performed for each different image to determine the terminal nucleotide for every microparticle. Where multiple nucleotides fluoresce at different wavelengths in a same image, the various different nucleotides may be determined for each microparticle by determining the emitting wavelength for each microparticle.

Regardless of how the terminal nucleotides are determined for the microparticles/associated oligonucleotides, the overall process may be repeated for each new terminal nucleotide. More specifically, after identifying the terminal nucleotides, they may be cleaved (e.g., using a restriction enzyme) and the process may be repeated for the new terminal nucleotide to determine the next nucleotide in the sequence.

After the sequences of the oligonucleotides of the microparticles have been determined, the entire sequence of the polynucleotide may be determined from the sequences of the oligonucleotides. This sequencing step may be performed by performing overlap analysis of the oligonucleotides (where the polynucleotide was initially cut into several different sets of overlapping oligonucleotides, e.g., resulting in multiple iterations of sequencing) or by comparing the sequences to a polynucleotide standard or known similar sequence, e.g., corresponding to the same species from which the polynucleotide was extracted.

FIGS. 4A-6—Exemplary Images Corresponding to an Embodiment of the Method

FIGS. 4A-6 are exemplary images corresponding to an embodiment of the method of FIG. 3. The particular details of the following descriptions and Figures are exemplary only and are not intended to limit the scope of the embodiments described herein.

Figure 4A:
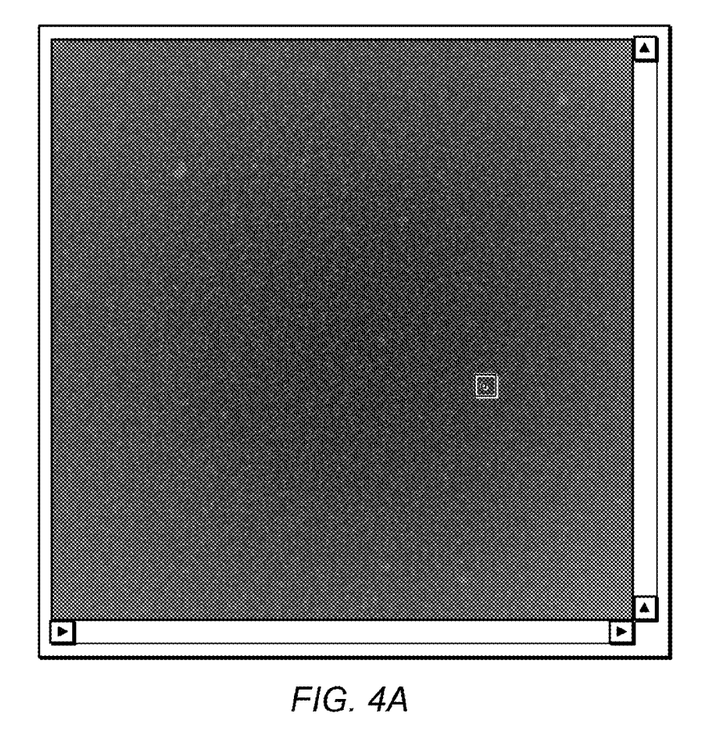

As discussed above, an initial image of the microparticles may be obtained. In some embodiments, the size of the reaction chamber or flowcell may be large enough that it is divided into a plurality of tiles. For example, the flowcell may be divided into 200 or so tiles. Accordingly, an image of each tile may be initially obtained. This image may be obtained by dividing an initial image of the entire flowcell or by capturing individual images, as desired.

Figure 4B:
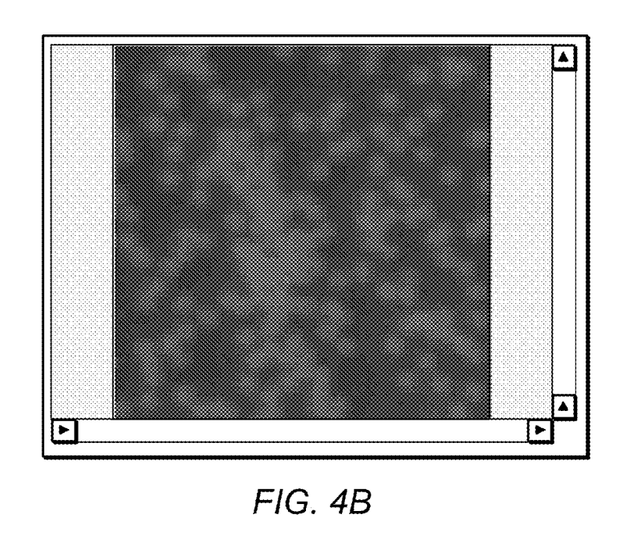

FIG. 4A illustrates an exemplary image of a tile of the flowcell. As shown, this image is a 2000×2000 grey scale image, without fluorescence. A small portion of FIG. 4A (shown as a box in FIG. 4A) is enlarged in FIG. 4B. Each of the small circular gray elements in this image corresponds to a microparticle. As shown, several of these microparticles are clumped together. As can be seen in FIG. 4B, the microparticle distribution is random but also unique. The particular portions of the image of FIG. 4A may be selected randomly or using entropy, among other possibilities.

Figure 5A:
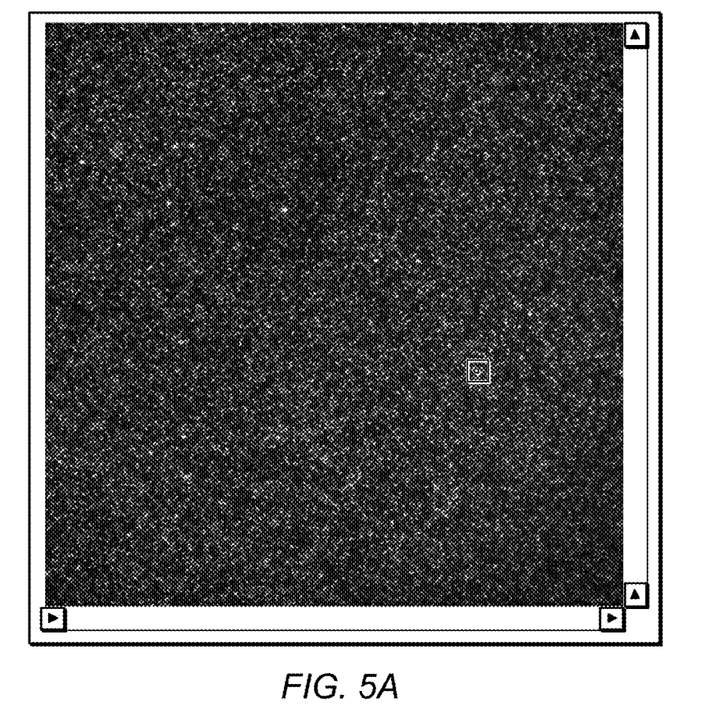

FIG. 5A illustrates a second image of the tile of FIG. 4A, except including fluorescing microparticles. This image was captured in a spectral range to take advantage of the florescence caused by the chemical reactions discussed above. The bright spots in the image represent fluorescing microparticles which have a terminal nucleotide of a specific type. In this example, there may be four of these images, one for each DNA nucleotide: A, T, C, and G.

Figure 5B:
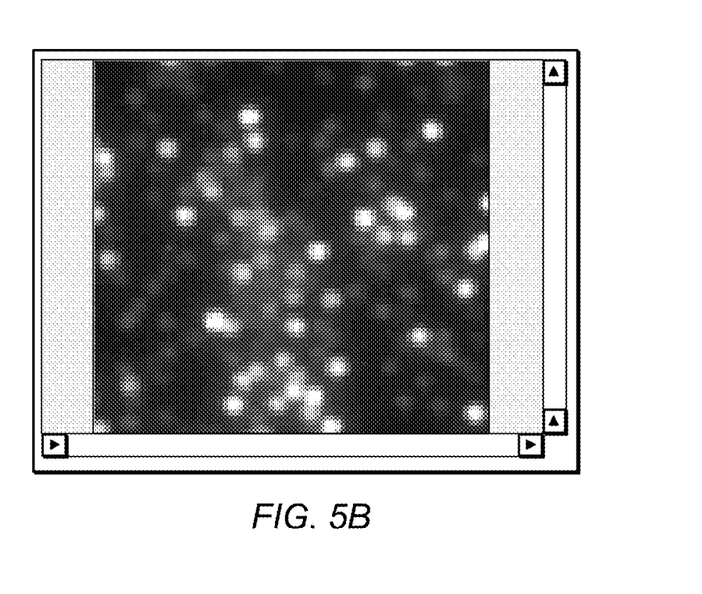

FIG. 5B illustrates corresponding smaller portion of FIG. 4B. As can be seen, although various ones of the microparticles are glowing, the unique pattern of FIG. 4B is still present in FIG. 5B and can be identified.

Figure 6:
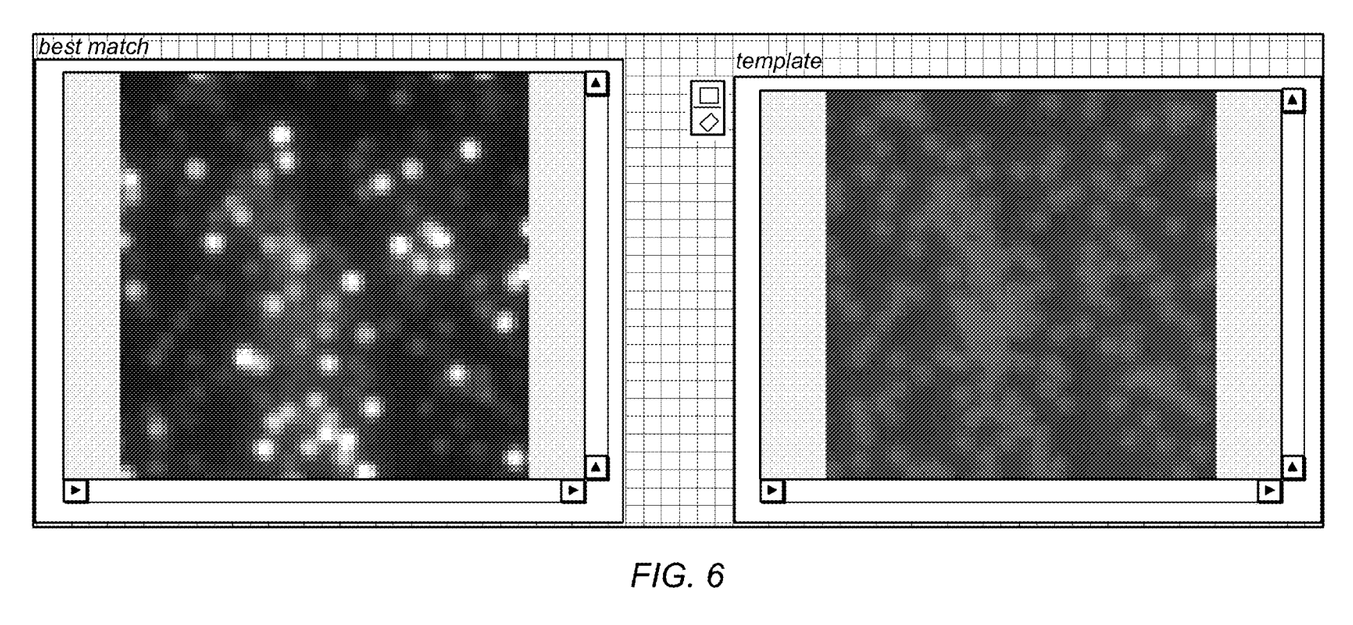

FIG. 6 illustrates a side by side comparison of FIGS. 4B and 5B. Using the pattern matching algorithms discussed above, the method may match these two portions in the two images. Once these fingerprint portions matched (e.g., for a plurality of different subportions), the method may be configured to match the microparticles for the full tile and correspondingly identify which of the microparticles in the first image are fluorescing in the second image, thereby allowing for identification of the particular terminal nucleotide for the glowing microparticles.

The method may be repeated for each nucleotide in the tile. That method may be repeated for each of the tiles in the flowcell. And finally, that entire method may be repeated for each nucleotide in the sequence of oligonucleotides in order to determine the sequence of the parent polynucleotide.

This matching process may be able to adjust for arbitrary shifts, rotation (e.g., +/−2 degrees), and scaling (e.g., +/−1%) in order to match the initial and subsequent images. Because the subportions are small, they may not suffer much from rotation/scaling effects. More specifically, the pattern matching algorithm may still be able to match the subportions (which may not be possible for larger portions) even when scaling and rotation of the subsequent image(s) differs from the original image. Additionally, this small size may mean that the pattern matching algorithm may be able to find the subportions quickly in subsequent images. Because of this efficient pattern matching, the rotation and scaling of the entire image may be quickly calculated using the matched subportions' location (e.g., suing 3-5 subportions). This efficiency may allow the pattern matching to be performed as quickly as the reaction takes place, which may dramatically increase the speed of the entire sequencing process. Thus, following embodiments described herein, the limiting factor may be the chemical reactions or image acquisition rather than the image processing step.

Further Embodiments

In the embodiments discussed above, small portions of the original image may be used as "fingerprints" in order to perform matching of the microparticles in the images. However, in alternative embodiments, actual unique elements or fiducials may be introduced to be used for identification and/or alignment instead of the smaller portions. For example, unique microparticles (e.g., larger than normal microparticles) or other objects may be introduced into the substrate which are uniquely identifiable. Accordingly, these fiducials may be used as an alternative to (or in addition to) the identified subportions for performing the microparticle matching.

Additionally, while the above embodiments focus on the use of microparticles, the oligonucleotides may also be loaded on other vehicles or may be attached to a fixed substrate, among other possibilities. However, the image processing discussed above may still apply to such embodiments.

Finally, while the above-described embodiments relate to the sequencing of polynucleotides, the same set of image processing functions may be used to perform pattern matching or image alignment for various other applications. For example, the embodiments described above may be particularly suitable for matching any sets of images which include randomly distributed elements, e.g., similar to the microparticles discussed above.

Although the embodiments above have been described in considerable detail, numerous variations and modifications will become apparent to those skilled in the art once the above disclosure is fully appreciated. It is intended that the following claims be interpreted to embrace all such variations and modifications.

We claim:

1. A computer-implemented method for performing sequencing of a polynucleotide, comprising:
   receiving, by the computer, a first image of microparticles, wherein the first image is stored in a memory of the computer, wherein the microparticles are distributed in a random fashion on a substrate wherein the microparticles have respective random positions on the substrate, wherein the respective random positions are not pre-determined and are not regularly spaced, and wherein each of the microparticles comprises a plurality of similar oligonucleotides of the polynucleotide;
   receiving, by the computer, a second image of the microparticles, wherein the second image of the microparticles highlights at least some of the microparticles in response to fluorescent chemicals attached to the oligonucleotides based on terminal nucleotides of the oligonucleotides on the microparticles, and wherein the second image is stored in the memory of the computer;
   determining, by the computer, a plurality of first subportions of the first image, wherein each subportion comprises a respective plurality of microparticles distributed in a random fashion, and wherein each first subportion's random distribution comprises a respective unique pattern;
   analyzing, by the computer, the second image to identify a plurality of second subportions in the second image that each corresponds to a respective one of the plurality of first subportions based on the respective unique patterns;
   matching, by the computer, a plurality of the microparticles in the first and second images based on said analyzing using the respective unique patterns; and
   determining, by the computer, the sequence of nucleotides of the polynucleotide based on said matching and the highlighted microparticles, wherein the sequence of nucleotides is stored in the memory of the computer.

2. The computer-implemented method of claim 1, wherein the first image and the second image differ in at least one of scale, rotation, or translation.

3. The computer-implemented method of claim 1, further comprising:
   modifying, by the computer, the second image to correspond to the first image based on said analyzing using geometric relationships between the first image and the second image.

4. The computer-implemented method of claim 3, wherein the first image has a first orientation, wherein said modifying comprises rotating the second image to match the first orientation of the first image based on said analyzing using the geometric relationships between the first image and the second image.

5. The computer-implemented method of claim 3, wherein the first image has a first scale, wherein said modifying comprises scaling the second image to match the first scale of the first image based on said analyzing using the geometric relationships between the first image and the second image.

6. The computer-implemented method of claim 1, wherein said determining the sequence of the nucleotides of the polynucleotide comprises determining sequences of nucleotides of the oligonucleotides of each of the microparticles.

7. The computer-implemented method of claim 6, wherein in the second image, a subset of the microparticles are illuminated corresponding to a chemical reaction used to identify one or more nucleotides of the oligonucleotides comprised on the microparticles, wherein the method further comprises:
   identifying, by the computer, the subset of the microparticles that are illuminated in the second image;
   wherein determining the sequence of nucleotides of the oligonucleotides of each of the microparticles is based on said identifying the subset of the microparticles that are illuminated in the second image.

8. The computer-implemented method of claim 1, further comprising:
   receiving, by the computer, a plurality of additional images of the microparticles;
   performing, by the computer, said analyzing and said matching for each of the plurality of additional images;
   wherein said determining the sequence of nucleotides is based on said performing.

9. The computer-implemented method of claim 1, further comprising:
   receiving, by the computer, a third image of the microparticles;
   receiving, by the computer, a fourth image of the microparticles;
   receiving, by the computer, a fifth image of the microparticles;
   performing, by the computer, said analyzing and said matching for each of the third, fourth, and fifth images of the microparticles;
   wherein the first image is an initial image of the microparticles, wherein the second image corresponds to a chemical reaction for identifying a first type of nucleotide, wherein the third image corresponds to a chemical reaction for identifying a second type of nucleotide, wherein the fourth image corresponds to a chemical reaction for identifying a third type of nucleotide, wherein the fifth image corresponds to a chemical reaction for identifying a fourth type of nucleotide;

wherein said determining the sequence of nucleotides of the polynucleotide comprises performing said receiving, said analyzing, and said matching for the second, third, fourth, and fifth images a plurality of times for a plurality of nucleotides of the oligonucleotides comprised on each of the microparticles.

10. The computer-implemented method of claim 9, wherein the chemical reactions for the different types of nucleotide cause illumination of the microparticles at respective, different wavelengths.

11. A non-transitory, computer accessible memory medium storing program instructions for performing sequencing of a polynucleotide, wherein the program instructions are executable to:

receive a first image of microparticles, wherein the microparticles are distributed in a random fashion on a substrate wherein the microparticles have respective random positions on the substrate, wherein the respective random positions are not pre-determined and are not regularly spaced, and wherein each of the microparticles comprise a plurality of similar oligonucleotides of the polynucleotide;

receive a second image of the microparticles, wherein the second image of the microparticles highlights at least some of the microparticles in response to fluorescent chemicals attached to the oligonucleotides based on terminal nucleotides of the oligonucleotides on the microparticles;

determine a plurality of first subportions of the first image, wherein each subportion comprises a respective plurality of microparticles distributed in a random fashion, and wherein each first subportion's random distribution comprises a respective unique pattern;

analyze the second image to identify a plurality of second subportions in the second image that each corresponds to a respective one of the plurality of first subportions based on the respective unique patterns;

match a plurality of the microparticles in the first and second images based on said analyzing using the respective unique patterns; and determine the sequence of nucleotides of the polynucleotide based on said matching and the highlighted microparticles.

12. The non-transitory, computer accessible memory medium of claim 11, wherein the first image and the second image differ in at least one of scale, rotation, or translation.

13. The non-transitory, computer accessible memory medium of claim 11, wherein the program instructions are further executable to:

modify the second image to correspond to the first image based on said analyzing using geometric relationships between the first image and the second image.

14. The non-transitory, computer accessible memory medium of claim 13, wherein the first image has a first orientation, wherein said modifying comprises rotating the second image to match the first orientation of the first image based on said analyzing using the geometric relationships between the first image and the second image.

15. The non-transitory, computer accessible memory medium of claim 13, wherein the first image has a first scale, wherein said modifying comprises scaling the second image to match the first scale of the first image based on said analyzing using the geometric relationships between the first image and the second image.

16. The non-transitory, computer accessible memory medium of claim 11, wherein said determining the sequence of the nucleotides of the polynucleotide comprises determining sequences of nucleotides of the oligonucleotides of each of the microparticles.

17. The non-transitory, computer accessible memory medium of claim 16, wherein in the second image, a subset of the microparticles are illuminated corresponding to a chemical reaction used to identify one or more nucleotides of the oligonucleotides comprised on the microparticles, wherein the program instructions are further executable to:

identify the subset of the microparticles that are illuminated in the second image;

wherein determining the sequence of nucleotides of the oligonucleotides of each of the microparticles is based on said identifying the subset of the microparticles that are illuminated in the second image.

18. The non-transitory, computer accessible memory medium of claim 11, wherein the program instructions are further executable to:

receive a plurality of additional images of the microparticles;

perform said analyzing and said matching for each of the plurality of additional images;

wherein said determining the sequence of nucleotides is based on said performing.

19. The non-transitory, computer accessible memory medium of claim 11, wherein the program instructions are further executable to:

receive a third image of the microparticles;
receive a fourth image of the microparticles;
receive a fifth image of the microparticles;
perform said analyzing and said matching for each of the third, fourth, and fifth images of the microparticles;

wherein the first image is an initial image of the microparticles, wherein the second image corresponds to a reaction for identifying a first type of nucleotide, wherein the third image corresponds to a reaction for identifying a second type of nucleotide, wherein the fourth image corresponds to a reaction for identifying a third type of nucleotide, wherein the fifth image corresponds to a reaction for identifying a fourth type of nucleotide;

wherein said determining the sequence of nucleotides of the polynucleotide comprises performing said receiving, said analyzing, and said matching for the second, third, fourth, and fifth images a plurality of times for a plurality of nucleotides of the oligonucleotides comprised on each of the microparticles.

20. The non-transitory, computer accessible memory medium of claim 19, wherein the chemical reactions for the different types of nucleotide cause illumination of the microparticles at respective, different wavelengths.

21. A system for performing sequencing of a polynucleotide, comprising:

an image acquisition apparatus, wherein the image acquisition apparatus is configured to acquire images of microparticles, wherein the microparticles are distributed in a random fashion on a substrate wherein the microparticles have respective random positions on the substrate, wherein the respective random positions are not pre-determined and are not regularly spaced, and wherein each of the microparticles comprise a plurality of similar oligonucleotides of the polynucleotide;

a processor coupled to the image acquisition device;
a memory medium coupled to the processor, wherein the memory medium stores program instructions that are executable by the processor to:
    receive a first image of microparticles via the image acquisition apparatus at a first time;
    receive a second image of the microparticles via the image acquisition apparatus at a second time wherein the second image of the microparticles highlights at least some of the microparticles in response to fluorescent chemicals attached to the oligonucleotides based on terminal nucleotides of the oligonucleotides on the microparticles;
    determine a plurality of first subportions of the first image, wherein each subportion comprises a respective plurality of microparticles distributed in a random fashion, and wherein each first subportion's random distribution comprises a respective unique pattern;
    analyze the second image to identify a plurality of second subportions in the second image that each corresponds to a respective one of the plurality of first subportions based on the respective unique patterns;
    match a plurality of the microparticles in the first and second images based on said analyzing using the respective unique patterns; and
    determine the sequence of nucleotides of the polynucleotide based on said matching and the highlighted microparticles.

22. The system of claim 21, further comprising:
a chemical reaction apparatus coupled to the image acquisition device, wherein the chemical reaction apparatus comprises the substrate comprising the microparticles, wherein the chemical reaction apparatus is configured to expose the microparticles to a plurality of chemical reactions to determine the sequence of nucleotides of the polynucleotide.

23. The system of claim 22, wherein the first image is of the microparticles prior to a first chemical reaction, wherein the second image is of the microparticles after the first chemical reaction, wherein the chemical reaction apparatus is configured to perform the first chemical reaction to identify at least a first type of nucleotide.

24. The system of claim 21, wherein the program instructions are executable by the processor to cause the chemical reaction apparatus to perform the plurality of chemical reactions.

25. The system of claim 21, wherein the first image and the second image differ in at least one of scale, rotation, or translation.

* * * * *